U S007150709B1

United States Patent
Schmidt et al.

(10) Patent No.: US 7,150,709 B1
(45) Date of Patent: Dec. 19, 2006

(54) WAX-LESS IMPLANT SYSTEM

(75) Inventors: Bruno Schmidt, 5836 Portsmouth Dr., Tampa, FL (US) 33615; Robert McKenzie, Tampa, FL (US)

(73) Assignee: Bruno Schmidt, Tampa, FL (US)

( * ) Notice: Subject to any disclaimer, the term of this patent is extended or adjusted under 35 U.S.C. 154(b) by 228 days.

(21) Appl. No.: 11/021,961

(22) Filed: Dec. 24, 2004

(51) Int. Cl.
*A61M 36/00* (2006.01)
*A61N 5/00* (2006.01)

(52) U.S. Cl. .......................................... 600/7
(58) Field of Classification Search ................ 600/1–8; 604/57–64
See application file for complete search history.

(56) References Cited

U.S. PATENT DOCUMENTS

| | | | | |
|---|---|---|---|---|
| 4,105,030 A | * | 8/1978 | Kercso | 604/506 |
| 4,263,910 A | * | 4/1981 | Pardekooper et al. | 604/60 |
| 5,281,197 A | * | 1/1994 | Arias et al. | 604/57 |
| 5,395,319 A | * | 3/1995 | Hirsch et al. | 604/60 |
| 6,221,003 B1 | * | 4/2001 | Sierocuk et al. | 600/7 |
| 6,402,677 B1 | * | 6/2002 | Jacobs | 600/7 |
| 6,569,077 B1 | * | 5/2003 | Schmidt | 600/7 |

* cited by examiner

Primary Examiner—John P. Lacyk
(74) Attorney, Agent, or Firm—Stanley M Miller

(57) ABSTRACT

A seeding needle lumen is adapted to receive a string of seeds and spacers. A dimple is formed in the seeding needle near its distal end and a protuberance formed by the dimple extends into the lumen. A hollow housing formed of a bio-absorbable, flexible and resilient material is positioned within the lumen in abutting relation to a trailing end of the protuberance. The hollow housing has an external diameter slightly less than a diameter of the lumen so that the hollow housing cannot slide past the protuberance and an internal diameter adapted to slidingly receive a seed or spacer positioned at a leading end of a string. The flexible and resilient material is momentarily deformable so that the hollow housing may squeeze past said protuberance when a stylet is maintained in a fixed position in abutting relation to a trailing end of the seeds and spacers when the seeding needle is withdrawn.

9 Claims, 1 Drawing Sheet

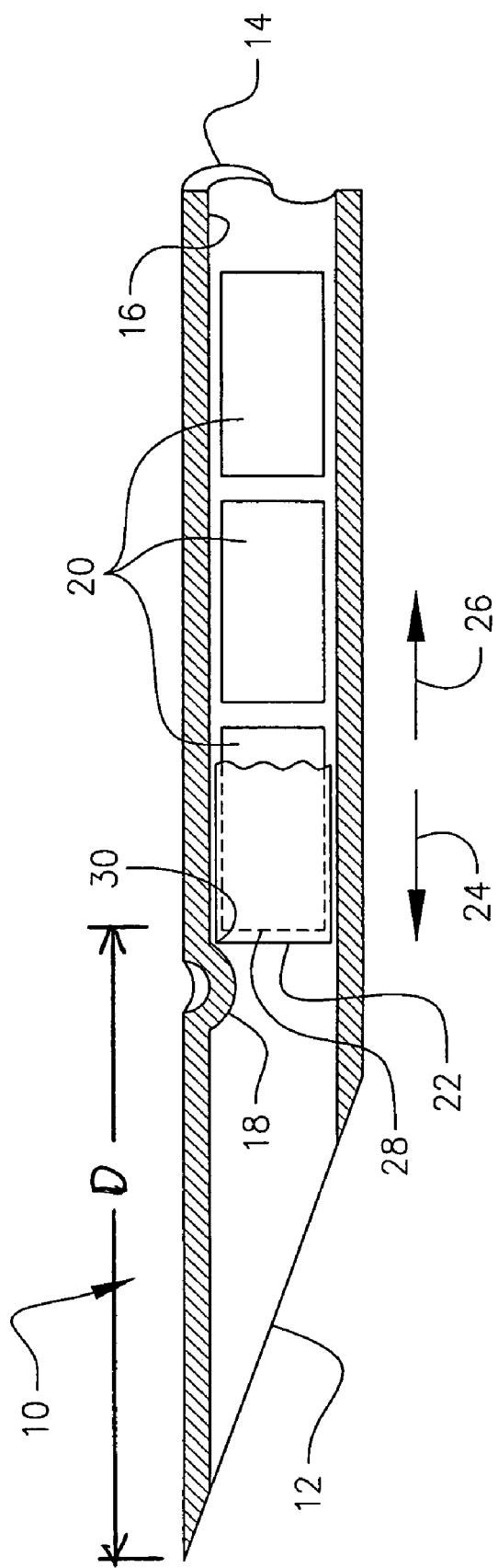
FIGURE

WAX-LESS IMPLANT SYSTEM

BACKGROUND OF THE INVENTION

1. Field of the Invention

This invention relates, generally, to needles used to implant radioactive seeds.

More particularly, it relates to a prostate seeding needle where a leading seed is housed in a bio-absorbable housing.

2. Description of the Prior Art

Radioactive seeds and spacers in a specific array are placed into a prostate in standard brachytherapy. The seeds and spacers are slidingly received within the lumen of a needle and the needle is inserted into the prostate. A stylet is introduced into the proximal end of the needle so that the leading end of the stylet abuts the trailing end of the last seed or spacer. The position of the stylet is maintained as the needle is retracted, thereby leaving the seeds and spacers in the prostate. The stylet is then removed along with the needle.

Bone wax is commonly used to plug the distal end of the needle to prevent the seeds and spacers from falling out of the needle during transport prior to use.

U.S. Pat. No. 6,569,077 to the present inventor discloses a seeding needle having a dimple formed near a distal end thereof. The dimple provides an interior protuberance that forms a barrier in the lumen. A flexible and resilient plug is placed at the distal end of a string of seeds and spacers. The flexible and resilient plug has a diameter greater than that of the string of seeds and spacers so that the dimple prevents unwanted proximal-to-distal travel of the plug and thus of the string behind it. When it is desired to deploy the seeds and spacers into a prostate, the seeding needle is introduced into the prostate to a predetermined position. A stylet positioned at the proximal end of the string is held in position while the seeding needle is retracted. The flexible and resilient plug is momentarily deformed as it squeezes past the restricting dimple. After the plug has squeezed past the protuberance, the plug and the string of seeds and spacers behind it are properly deployed as the seeding needle is fully withdrawn along with the stylet.

Thus, the protuberance formed by the dimple supplants the bone wax of the prior art. This makes the distance between the first seed and the distal end of the needle more uniform than was obtainable using only bone wax as a seed and spacer retention means.

It is desirable for the first seed to be as close as possible to the distal end of the needle, allowing precise placement of the first seed. The only drawback of the above-described wax-less system is that the first seed in the string is spaced from the distal end of the seeding needle by a distance equal to the length of the protuberance from the distal end of the seeding needle, plus the length of the plug itself. For example, if the retaining plug is 0.040–0.080 inches in length, the first seed is that distance behind the dimple. Accordingly, precision is lost as to exactly where the first seed is in relation to the distal tip of the seeding needle.

The distance variation caused by the use of bone wax is thus substantially reduced, but the plug itself also introduces a distance variation.

Thus there is a need for an improved system that does not rely upon bone wax or the flexible and resilient plug.

However, in view of the prior art considered as a whole at the time the present invention was made, it was not obvious to those of ordinary skill in the pertinent art how such need could be fulfilled.

SUMMARY OF THE INVENTION

The long-standing but heretofore unfulfilled need for a wax-less implant system where the position of a first seed in a string of seeds and spacers can be known with precision is now met by a new, useful, and nonobvious invention. The novel wax-less implant system for deploying seeds and spacers in tissue includes an elongate seeding needle having a lumen adapted to slidingly receive therein a string of seeds and spacers. A dimple is formed in the elongate seeding needle near a distal end thereof. A protuberance created by the dimple extends into the lumen. The protuberance has a leading end positioned near the distal end of the elongate seeding needle and has a trailing end spaced proximal to the leading end by a distance equal to the length of the dimple.

A material build-up is affixed to the first seed or spacer. This can be in the form of a flexible and resilient material or a brittle, easily shattered material such as a cyanoacrylate coating. Both will deform or break away when forced past the protuberance. The flexible and resilient material is the preferred embodiment and will be discussed here in the form of a hollow housing.

A hollow housing formed of a flexible and resilient material is positioned within the lumen in abutting relation to the trailing end of the protuberance. The hollow housing has an external diameter only slightly less than a diameter of the lumen so that the hollow housing cannot slide past the protuberance under gravitational force, i.e., an external force greater than gravitational force must be applied thereto. The hollow housing has an internal diameter adapted to slidingly receive a seed positioned at a leading end of a string of seeds and spacers. The flexible and resilient material from which the hollow housing is made is momentarily deformable so that the hollow housing may squeeze past the protuberance when a stylet is maintained in a fixed position in abutting relation to a trailing end of the seeds and spacers when the elongate seeding needle is withdrawn.

The hollow housing is formed of a nontoxic bio-absorbable material so that it is absorbed by the body, leaving only the seeds and spacers in the prostate or other tissue. It has a wall thickness of 0.002" to 0.004" thus allowing the first seed to be 0.002" to 0.004" from the dimple instead of the 0.040" to 0.080" depending on the plug length.

The novel method for deploying seeds and spacers in tissue includes the steps of providing an elongate seeding needle, adapting a lumen of the elongate seeding needle to slidingly receive therein a string of seeds and spacers, forming a dimple in the elongate seeding needle near a distal end thereof, thereby forming a protuberance that extends into the lumen, positioning a leading end of the protuberance near the distal end of the elongate seeding needle, positioning a trailing end of the protuberance spaced proximal to the leading end by a distance equal to the length of the dimple, positioning a hollow housing formed of a flexible and resilient material within the lumen in abutting relation to the trailing end of the protuberance, dimensioning the hollow housing to have an external diameter only slightly less than a diameter of the lumen so that the hollow housing cannot slide past the protuberance under gravitational force, dimensioning the hollow housing to have an internal diameter adapted to slidingly receive a seed or spacer positioned at a leading end of a string of seeds and spacers, and momentarily deforming the flexible and resilient material from which the hollow housing is made so that the hollow housing squeezes past the protuberance housing when a stylet is maintained in a fixed position in abutting relation to a trailing end of the seeds and spacers when the elongate seeding needle is withdrawn. The housing may alternatively be placed over the first seed or spacer in the string of seeds and spacers prior to insertion of the first seed or spacer into the lumen of the needle.

In an alternate embodiment of the invention, the hollow housing is replaced by a brittle and easily shattered coating on the first seed or spacer, such that when forced past the protuberance, it shatters and allows the string of seeds and spacers to pass the protuberance. The coating on the first seed or spacer is created to have an external diameter only slightly less than a diameter of the lumen so that the coated first seed or spacer cannot slide past the protuberance under gravitational force.

In yet another alternate embodiment of the invention, the hollow housing is replaced by a flexible and resilient coating on the first seed or spacer. The first coated seed or spacer would be inserted before the rest of the string of seeds and spacers. The rest of the operation and would be the same as with the hollow housing.

An important object of this invention is to provide a system for making uniform the distance between a first seed or spacer and the distal end of a needle.

A closely related object is to provide such a system that does not rely upon bone wax.

Another closely related object is to provide such a system that does not rely upon a flexible and resilient plug that may have a varying length.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

The FIGURE is a longitudinal sectional view of an illustrative embodiment of the invention.

DETAILED DESCRIPTION OF THE PREFERRED EMBODIMENT

Referring to the FIGURE, it will there be seen that the reference numeral 10 denotes an illustrative embodiment of the present invention as a whole.

Seeding needle 10 includes a beveled distal end 12 and a proximal end, not depicted, that lies proximally of the point 14 where the FIGURE is cut off to enable provision of a more detailed view of the distal end of the needle.

The lumen of seeding needle 10 is denoted 16.

Dimple 18 is formed in said seeding needle by suitable means. The interior of the dimple creates a protrusion or protuberance 18 that extends into lumen 16 as depicted. A disclosure of how such dimple, or other protuberance, is formed in needle 10 is provided in U.S. Pat. No. 6,569,077, entitled "Dimpled Seed Implant Needle," awarded May 27, 2003, to the present inventor. Said patent is hereby incorporated into this disclosure by reference.

Seeds and spacers, collectively denoted 20, are positioned in lumen 16 on the proximal side of protuberance 18. Note that the diameter of the seeds and spacers is less then the diameter of lumen 16 and less than the diameter of lumen 16 as decreased by protuberance 18. In other words, the common diameter of said seeds and spacers is sufficiently small to enable said seeds and spacers to slide from lumen 16 unimpeded by protuberance 18.

Accordingly, in the prior art patent referenced herein, a flexible and resilient plug having a diameter that prevented, in the absence of externally applied force, said plug from sliding past protuberance 18 was placed at the distal end of the string of seeds and spacers so that said string could not slide past protuberance 18 unless a stylet was positioned at the trailing end of the string while needle 12 was withdrawn, thereby causing the flexible and resilient plug to momentarily deform as it squeezes past the protuberance. When the plug was thus squeezed past the protuberance, no further resistance to deployment from lumen 16 was presented to the seeds and spacers as the needle was withdrawn.

In the present invention, no bone wax or flexible and resilient plug is provided. Instead, a hollow housing 22 of flexible and resilient construction is employed. The external diameter of hollow housing 22 is such that it cannot slide past protuberance 18 in a proximal-to-distal direction 24 under the force of gravity but it has a flexibility and resilience much like that of the prior art plug that enables it to be momentarily compressed so that housing 22 can squeeze past protuberance 18 when needle 10 is withdrawn in a distal-to-proximal direction 26 while a stylet prevents distal-to-proximal travel of the seeds and spacers.

Hollow housing 22 may be formed of a non-toxic, bio-absorbable material so that it is absorbed by the body after deployment or by a non-toxic inert material that remains inside the body.

The hollow structure of housing 22 enables leading end 28 of the first seed in the string of seeds and spacers to be positioned in substantial alignment with the proximal or trailing end 30 of protuberance 18. In the FIGURE, the spacing between leading end 28 of said first seed and said proximal end 30 of protuberance 18 is slightly exaggerated to clarify the drawing.

The exact distance D from the distal end of needle 10 to the proximal end of protuberance 18 is known. Accordingly, distance D may be taken as the distance from said needle distal end to leading end 28 of the first seed in the string of seeds and spacers. This eliminates the ambiguity created by bone wax and by the flexible and resilient, non-hollow plug of the prior art.

The length of the housing 22 may, but is not so limited, cover the first part of the first seed or spacer or may cover the entire string of seeds and spacers.

In an alternate embodiment of the invention not shown in the drawings, the hollow housing is replaced by a brittle and easily shattered coating on the first seed or spacer, such that when forced past the protuberance, it shatters and allows the string of seeds and spacers to pass the protuberance. The coating on the first seed or spacer is created to have an external diameter only slightly less than a diameter of the lumen so that the coated first seed or spacer cannot slide past the protuberance under gravitational force.

In yet another alternate embodiment of the invention not shown in the drawings, the hollow housing is replaced by a flexible and resilient coating on the first seed or spacer. The first coated seed or spacer would be inserted before the rest of the string of seeds and spacers. The rest of the operation would be the same as the embodiment with the hollow housing.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,

What is claimed is:

1. A wax-less implant system for deploying seeds and spacers in tissue, comprising:
    an elongate seeding needle;
    said elongate seeding needle having a lumen adapted to slidingly receive therein a string of seeds and spacers;
    a dimple formed in said elongate seeding needle near a distal end thereof;
    a protuberance that extends into said lumen, said protuberance created by said dimple;
    said protuberance having a leading end positioned near said distal end of said elongate seeding needle and having a trailing end spaced proximal to said leading end by a distance equal to the length of said dimple;
    a hollow housing formed of a flexible and resilient material being positioned within said lumen in abutting relation to said trailing end of said protuberance;
    said hollow housing having an external diameter only slightly less than a diameter of said lumen so that said hollow housing cannot slide past said protuberance under gravitational force;
    said hollow housing having an internal diameter adapted to slidingly receive a seed or spacer positioned at a leading end of a string of seeds and spacers;
    said flexible and resilient material from which said hollow housing is made being momentarily deformable so that said hollow housing may squeeze past said protuberance when a stylet is maintained in a fixed position in abutting relation to a trailing end of said seeds and spacers when said elongate seeding needle is withdrawn.

2. The system of claim 1, further comprising:
    said hollow housing being formed of a bio-absorbable material.

3. The system of claim 1, wherein the housing may, but is not so limited, cover the first part of the first seed or spacer or may cover the entire string of seeds and spacers.

4. A method for deploying seeds and spacers in tissue, comprising:
    providing an elongate seeding needle;
    adapting a lumen of said elongate seeding needle to slidingly receive therein a string of seeds and spacers;
    forming a dimple in said elongate seeding needle near a distal end thereof;
    forming a protuberance that extends into said lumen, said protuberance formed by said dimple;
    positioning a leading end of said protuberance near said distal end of said elongate seeding needle and positioning a trailing end of said protuberance spaced proximal to said leading end by a distance equal to the length of said dimple;
    positioning a hollow housing formed of a flexible and resilient material within said lumen in abutting relation to said trailing end of said protuberance;
    dimensioning said hollow housing to have an external diameter only slightly less than a diameter of said lumen so that said hollow housing cannot slide past said protuberance under gravitational force;
    dimensioning said hollow housing to have an internal diameter adapted to slidingly receive a seed or spacer positioned at a leading end of a string of seeds and spacers;
    loading said seeds and spacers into the lumen of the needle;
    momentarily deforming said flexible and resilient material from which said hollow housing is made so that said hollow housing may squeeze past said protuberance when a stylet is maintained in a fixed position in abutting relation to a trailing end of said seeds and spacers when said elongate seeding needle is withdrawn.

5. The method of claim 4, further comprising:
    forming said hollow housing of a bio-absorbable material.

6. The method of claim 4 further comprising:
    placing the housing over the first seed or spacer in the string of seeds and spacers prior to insertion of the first seed or spacer into the lumen of the needle.

7. A wax-less implant system for deploying seeds and spacers in tissue, comprising:
    an elongate seeding needle;
    said elongate seeding needle having a lumen adapted to slidingly receive therein a string of seeds and spacers;
    a dimple formed in said elongate seeding needle near a distal end thereof;
    a protuberance that extends into said lumen, said protuberance created by said dimple;
    said protuberance having a leading end positioned near said distal end of said elongate seeding needle and having a trailing end spaced proximal to said leading end by a distance equal to the length of said dimple;
    a brittle and easily shattered coating on the leading end of the first seed or spacer being positioned within said lumen in abutting relation to said trailing end of said protuberance;
    said coated first seed or spacer having an external diameter only slightly less than a diameter of said lumen so that said coated first seed or spacer cannot slide past said protuberance under gravitational force;
    said coated first seed or spacer when forced past the protuberance shatters and allows the string of seeds or spacers to pass the protuberance when a stylet is maintained in a fixed position in abutting relation to a trailing end of said seeds and spacers when said elongate seeding needle is withdrawn.

8. A method for deploying seeds and spacers in tissue, comprising:
    providing an elongate seeding needle;
    adapting a lumen of said elongate seeding needle to slidingly receive therein a string of seeds and spacers;
    forming a dimple in said elongate seeding needle near a distal end thereof;
    forming a protuberance that extends into said lumen, said protuberance formed by said dimple;
    positioning a leading end of said protuberance near said distal end of said elongate seeding needle and positioning a trailing end of said protuberance spaced proximal to said leading end by a distance equal to the length of said dimple;

positioning a first seed or spacer having a brittle but easily shattered coating on its leading end within said lumen in abutting relation to said trailing end of said protuberance;

dimensioning said brittle coating on said first seed or spacer to have an external diameter only slightly less than a diameter of said lumen so that said brittle coated first seed or spacer cannot slide past said protuberance under gravitational force;

loading the remainder of said seeds and spacers into the lumen of the needle;

shattering said brittle coating of said first seed or spacer so that said protuberance passes over said seed or spacer when a stylet is maintained in a fixed position in abutting relation to a trailing end of said seeds and spacers when said elongate seeding needle is withdrawn.

9. A wax-less implant system for deploying seeds and spacers in tissue, comprising:

an elongate seeding needle;

said elongate seeding needle having a lumen adapted to slidingly receive therein a string of seeds and spacers;

a dimple formed in said elongate seeding needle near a distal end thereof;

a protuberance that extends into said lumen, said protuberance created by said dimple;

said protuberance having a leading end positioned near said distal end of said elongate seeding needle and having a trailing end spaced proximal to said leading end by a distance equal to the length of said dimple;

a flexible and resilient material coating on the leading end of the first seed or spacer being positioned within said lumen in abutting relation to said trailing end of said protuberance;

said coated first seed or spacer having an external diameter only slightly less than a diameter of said lumen so that said coated first seed or spacer cannot slide past said protuberance under gravitational force;

said flexible coated first seed or spacer when forced past the protuberance being momentarily deformable so that said coated first seed or spacer may squeeze past said protuberance when a stylet is maintained in a fixed position in abutting relation to a trailing end of said seeds and spacers when said elongate seeding needle is withdrawn.

* * * * *